United States Patent [19]

Matteson et al.

[11] Patent Number: 5,817,882

[45] Date of Patent: Oct. 6, 1998

[54] STEREOCONTROLLED SYNTHESIS OF SERRICORNIN

[75] Inventors: Donald S. Matteson; Rajendra P. Singh, both of Moscow, Id.

[73] Assignee: Washington State University Research Foundation, Pullman, Wash.

[21] Appl. No.: 923,174

[22] Filed: Sep. 4, 1997

[51] Int. Cl.$^6$ .................................................. C07C 45/00
[52] U.S. Cl. ........................................ 568/404; 568/909.5
[58] Field of Search ................................. 568/404, 909.5

[56] References Cited

U.S. PATENT DOCUMENTS 4,525,309  6/1985  Matteson et al. .................... 260/462

OTHER PUBLICATIONS

Kuwahara, Y. et al., "Chemical Studies on the Anobiidae: Sex Pheromone of the Drugstore Beetle, Stegobium Paniceum (L.) (Coleoptera)," *Tetrahedron*, 34:1769–1774 (1978).

Mori, M. et al., "Inhibitory Action of (4S,6S,7R)–Isomer to Pheromonal Activity of Serricornin, (4S,6S, 7S)–7–Hydroxy–4,6–Dimethyl–3–Nonanone," *J. Chem. Ecol.*, 12(1):83–89 (1986).

Mori, K. and Watanabe, H., "A New Synthesis of Serricornin [(4S,6S,7S)–7–Hydroxy–4,6–Dimethyl–3–Nonanone], The Sex Pheromone of the Cigarette Beetle," *Tetrahedron*, 41(16):3423–3428 (1985).

Tripathy, P.B. and Matteson, D.S., "Asymmetric Synthesis of the Four Stereoisomers of 4–Methyl–3–heptanol via Boronic Esters: Sequential Double Stereodifferentiation Leads to Very High Purity," *Synthesis*, 3:200–206 (1990).

Sadhu, K.M. and Matteson, D.S., "(Chloromethyl)lithium: Efficient Generation and Capture by Boronic Esters and a Simple Preparation of Diisopropyl (Chloromethyl)boronate," *Organometallics*, 4:1687–1689 (1985).

Matteson, D.S. and Man, H.–W., "Enantioselective Capture and Retroracemization of (1–Bromoalkyl)boronic Esters by an N–Propanoyloxazolidinone Enolate and Iodide Ion,"*J. Org. Chem.*, 59:5734–5741 (1994).

Pappo, R. et al., "Osmium Tetroxide–Catalyzed Periodate Oxidation of Olefinic Bonds," *J. Org. Chem.*, 21:478–479 (1956).

Matteson et al., J. Am. Chem. Soc., 108:812–819, 1986.

*Primary Examiner*—Joseph McKane
*Assistant Examiner*—Taofiq A. Solola
*Attorney, Agent, or Firm*—Christensen, O'Connor, Johnson & Kindness

[57] ABSTRACT

Serricornin, the attractant pheromone of the cigarette beetle, is synthesized in high enantiomeric and diastereomeric purity via a series of reactions of asymmetric 2-(1-haloalkyl)-1,3,2-dioxaborolanes with Grignard reagents, which lead to the key intermediate [,S-(R*,R*,R*)]-2-ethyl-3,5-dimethyl-1-octen-6-ol. Oxidative cleavage of the carbon-carbon double bond of [S-(R*,R*,R*)]-2-ethyl-3,5-dimethyl-1-octen -6-ol with osmium tetroxide and sodium periodate yields serricornin.

7 Claims, No Drawings

STEREOCONTROLLED SYNTHESIS OF SERRICORNIN

Work leading to the present invention was supported by the Washington Technology Center.

This application claims the benefit of U.S. Provisional Application No. 60/024,694, filed Sep. 6, 1996, now abandoned.

FIELD OF THE INVENTION

This invention relates to the stereocontrolled asymmetric synthesis of serricomin, the attractant pheromone of the "cigarette beetle," *Lasioderma serricorne* F. (Anobiidae), a pest of dried foodstuffs and tobacco.

BACKGROUND OF THE INVENTION

The pheromone of the cigarette beetle, *Lasioderma serricorne* F. (Anobiidae), a pest of dried foodstuffs and tobacco, is (4S,6S,7S)-7-hydroxy-4,6-dimethyl-nonanone (1) [Kuwahara, Y. et al., *Tetrahedron*, 1978, 34:1769–1774; Mori, M. et al., *J Chem. Ecol.*, 1985, 12:83–89], also known as serricomin. Serricomin exists as an equilibrium mixture of the open chain keto alcohol 1 and its cyclic hemiacetal tautomer 2:

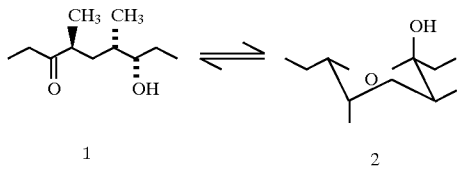

Stereoisomers of serricomin (1) include the following:

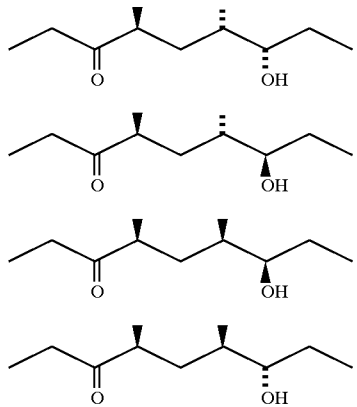

The attractant activity of serricomin is inhibited by the (4S,6S,7R)-isomer (3) at the 10% level, but the (4S,6R,7R)-isomer (4) and the (4S,6R,7S)-isomer (5) have no apparent effect up to a 1:1 ratio. A previous synthesis from microbially produced methyl (R)-3-hydroxypentanoate yielded 7.6% of 1 after numerous steps [Mori, K. and Watanabe, H., *Tetrahedron*, 1985, 41:3423–3428].

In order to synthesize an active attractant for control of these insect pests, it is clearly necessary to exclude the (4S,6S,7R)-isomer (3). In addition to the four stereoisomers shown above, there are four enantiomers of these, which are presumed to be inert. Thus, only one of eight stereoisomers, serricornin (1), is an active attractant. It is necessary to achieve a high degree of stereocontrol in order to synthesize serricornin (1) that does not contain any significant amount of the inhibitory diastereomer (3), and desirable to keep the proportions of the other six stereoisomers at a low level so as not to dilute the active material.

SUMMARY OF THE INVENTION

In one aspect of the present invention, a process is provided for preparing serricornin in high diastereomeric and enantiomeric purity. The basic synthetic method used for construction of the asymmetric stereocenters has been described previously [Matteson, D. S. and Sadhu, K. M., U.S. Pat. No. 4,525,309, Jun. 25, 1985; Matteson, D. S. et al., *J. Am. Chem. Soc.*, 1986, 108:812–819]. Particularly high diastereoselection results from the use of a chiral director which has $C_2$ symmetry [Tripathy, P. B. and Matteson, D. S., *Synthesis*, 1990, 200–206].

In a preferred embodiment, a sequence of highly stereoselective carbon chain extensions of asymmetric boronic esters with (dihalomethyl)lithium is used to establish all of the stereocenters of serricornin, which is an equilibrium mixture of structures 1 and 2. An outline of a practical synthesis is illustrated below, starting from an (R)-[4α,5β]-4,5-dialkyl-2-methyl-1,3,2-dioxaborolane (6), in which the alkyl groups $R^1$ are, for example, cyclohexyl groups.

Chain extensions are carried out according to an established procedure [Matteson, D. S. and Sadhu, K. M., U.S. Pat. No. 4,525,309, Jun. 25, 1985]. The chloro boronic ester 7 reacts with the Grignard reagent 8 (in which for example $R^2 = R^3 = H$) to produce an intermediate 9 having the correct stereochemistry in high purity (>98%). Further chain extensions and reactions with Grignard reagents lead via structures 10 and 12 to intermediate boronic ester 14, in which all of the stereochemistry of serricomin has been established. Oxidative deboronation with hydrogen peroxide yields intermediate 15, which can be generally described as an [S-(R*,R*,R *)]-7-alkylidene-4,6-dimethyl-3-nonanol or, alternatively, [3S,4S,6S)]-7-alkylidene-4,6-dimethyl-3-nonanol.

A key feature of this invention is the use of intermediate 15 as the immediate precursor to serricornin. Cleavage of the carbon-carbon double bond of 15 under mild conditions, for example the known oxidation by sodium periodate in the presence of a catalytic amount of osmium tetroxide or, alternatively, ozonolysis, generates the ketone functionality of serricornin (1) without disturbing the stereocenters.

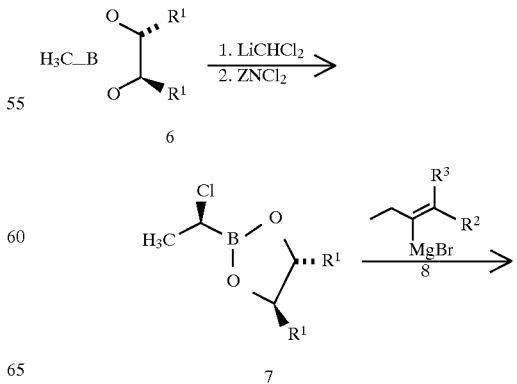

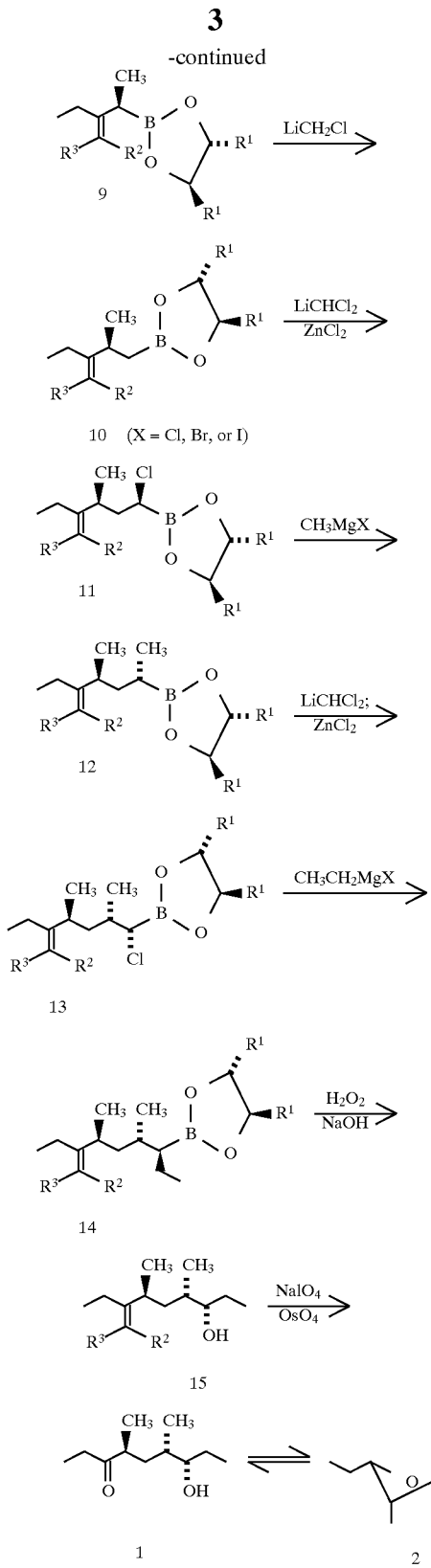

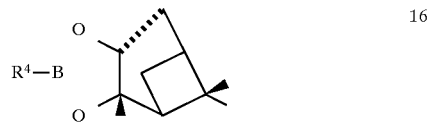

The exact nature of the groups $R^1$, $R^2$, and $R^3$ is not essential to this invention. $R^1$ may be any of several alkyl groups, including methyl or isopropyl as well as the aforementioned cyclohexyl group. $R^2$ and $R^3$ may be alkyl, aryl, or hydrogen, and may be the same or different.

In another preferred embodiment, pinanediol boronic esters are used in place of structures 6, 7, 9, 10, 12, and 14, and deboronation of the pinanediol analog of 14 with hydrogen peroxide yields 15. This series is summarized by structure 16, in which the group $R^4$ corresponds to the same series of substituents as those attached to boron in the sequence illustrated above.

The present invention allows the construction of the ketone function adjacent to a stereocenter in a new and efficient manner that is particularly useful in achieving the correct relationship to the other two stereocenters of serricomin. This synthesis provides serricomin that is not diluted by its enantiomer or other stereoisomers, and in particular does not contain any significant amount of the stereoisomer that inhibits attractant activity.

Serricornin is useful for attracting cigarette beetles into traps in order to detect infestations by these pests and to control their populations.

DETAILED DESCRIPTION OF THE PREFERRED EMBODIMENT

In a preferred embodiment, [4R-(4α,5β)]-4,5-dicyclohexyl-2-methyl-1,3,2-dioxaborolane (6) and (dichloromethyl)lithium react to yield [4R-[2(S*),4α,5β]]-4,5-dicyclohexyl-2-(1-chloroethyl)-1,3,2-dioxaborolane (7). This reaction is known to occur in two stages, and the second stage is promoted by zinc chloride [Matteson, D. S. and Sadhu, K. M., U.S. Pat. No. 4,525,309, Jun. 25, 1985; Matteson, D. S. et al., *J. Am. Chem. Soc.*, 1986, 108:812–819]. Reaction of 7 with (1-buten-2-yl)magnesium bromide (8a) yields [4R-[2(R*),4α,5β]]-4,5-dicyclohexyl-2-(2-ethyl-3-methylpropen-3-yl)-1,3,2-dioxaborolane (9a). The overall process of converting a boronic ester of a diol of $C_2$ symmetry [i.e., a (4α,5β)-4,5-dialkyl-2-alkyl-1,3,2-dioxaborolane] to a chloro boronic ester using the reaction with (dichloro-methyl)lithium, followed by replacement of the chloride with an alkyl group from a Grignard or lithium reagent, is known to yield a single diastereoisomer of >99% purity in several instances [Tripathy, P. B. and Matteson, D. S., *Synthesis*, 1990, 200–206].

Reaction with (chloromethyl)lithium [Sadhu, K. M. and Matteson, D. S., *Organometallics*, 1985, 4:1687–1689] converts 9a to [4R-[2(S*),4α,5β]]-4,5-dicyclohexyl-2-(2-ethyl-3-methylbuten-4-yl)-1,3,2-dioxaborolane (10a). Reaction of 10a with (dichloromethyl)lithium, then zinc chloride, yields [4R-[2(S*,S*),4α,5β]]-4,5-dicyclohexyl-2-(5-chloro-2-ethyl-3-methylpenten-5-yl)-1,3,2-dioxaborolane (11a), which with methylmagnesium chloride yields [4R-[2(S*,S*), 4α,5β]]-4,5-di-cyclohexyl-2-(2-ethyl-3,5-dimethylpenten-5-yl)-1,3,2-dioxaborolane (12a). Reaction of 12a with (dichloromethyl)lithium, then zinc chloride, yields [4R-[2(S*,S*,S*),4α,5β]]-4,5-dicyclohexyl-2-(6-chloro-2-ethyl-3,5-dimethylhexen-6-yl)-1,3,2-dioxaborolane (13a), which with ethylmagnesium bromide yields [4R-[2(S*,S*,S*),4α,5β]]-4,5-dicyclohexyl-2-(2,6-diethyl-3,5-dimethylhexen-6-yl)-1,3,2-dioxaborolane (14a).

Oxidation of 14a with alkaline hydrogen peroxide yields [S-(R*,R*,R*)]-2-ethyl-3,5-dimethyl-1-octen-6-ol (15a) (alternative name: [S-(R*,R*,R*)]-7-methylidene-4,6-dimethyl-3-nonanol). Cleavage of the double bond of 15a with sodium periodate in the presence of a catalytic amount of osmium tetroxide yields [S-(R*,R*,R*)-7-hydroxy-4,6-dimethylnonanone (1), which exists in equilibrium with its cyclic tautomer 2 and has been identified as serricornin [Kuwahara, Y. et al., *Tetrahedron*, 1978, 34:1769–1774; Mori, M. etal., *J Chem. Ecol.*, 1985, 12:83–89].

the conversion of 6 to 14. Thus, 17 with (dichloromethyl) lithium yields pinanediol (1S)-(1-chloroethyl)boronate (18) {systematic name {3aS-[2(R*),3aα,4β,6β,7aα]}-2-(1-chloroethyl)hexahydro-3a, 5,5-trimethyl-4,6-methano-1,3,2-benzodioxaborole}, a reaction analogous to the conversion of 6 to 7. The remaining steps to synthesize [S-(R*,R*,R*)]-2-ethyl-3, 5-dimethyl-1-octen-6-ol (15a) are similarly analogous to the process described above, with 19 in place of 9, 20 in place of 10, 21 in place of 12, and 22 in

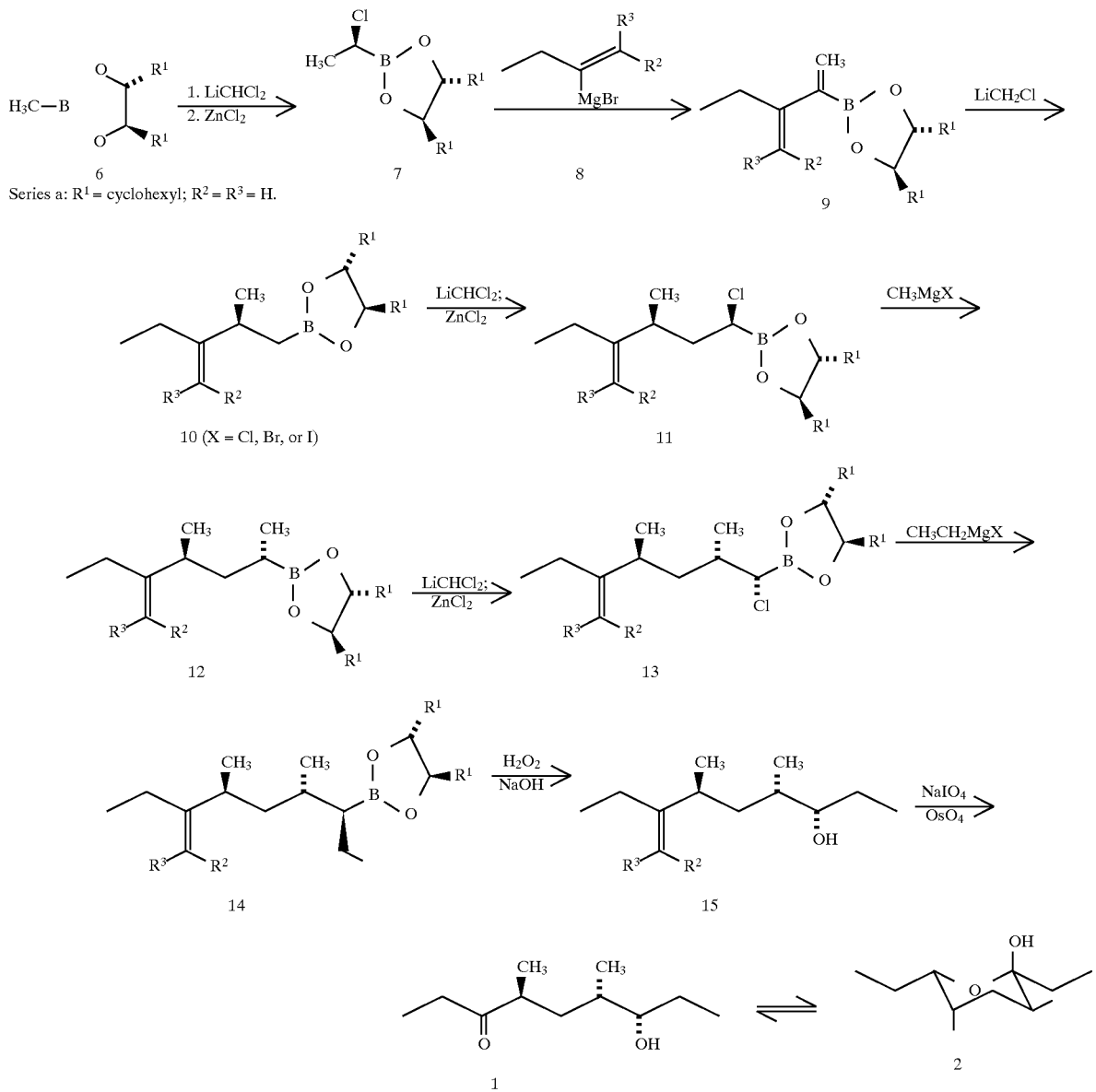

In another preferred embodiment, pinanediol {systematic name: [1S-(1α,2β,3β,5α)]-2,6,6-trimethyl-bicyclo[3.1.1] heptane-2,3-diol}, is used as the chiral director, and a sequence of boronic esters starting from pinanediol methylboronate (17) {systematic name {3aS-[3aα,4β,6β,7aα]}-2-(methyl) -hexahydro-3a,5,5-trimethyl-4,6-methano-1,3,2-benzodioxaborole} is synthesized in an analogous manner to place of 14. Although the stereoselectivity achieved with boronic esters of pinanediol, usually 98–99% [Matteson, D. S. and Sadhu, K. M., U.S. Pat. No. 4,525,309, Jun. 25, 1985], is not as high as that observed with boronic esters of $C_2$ symmetrical diols, it is sufficient for purposes of producing serricomin of high quality, and pinanediol is a relatively economical asymmetric diol to produce.

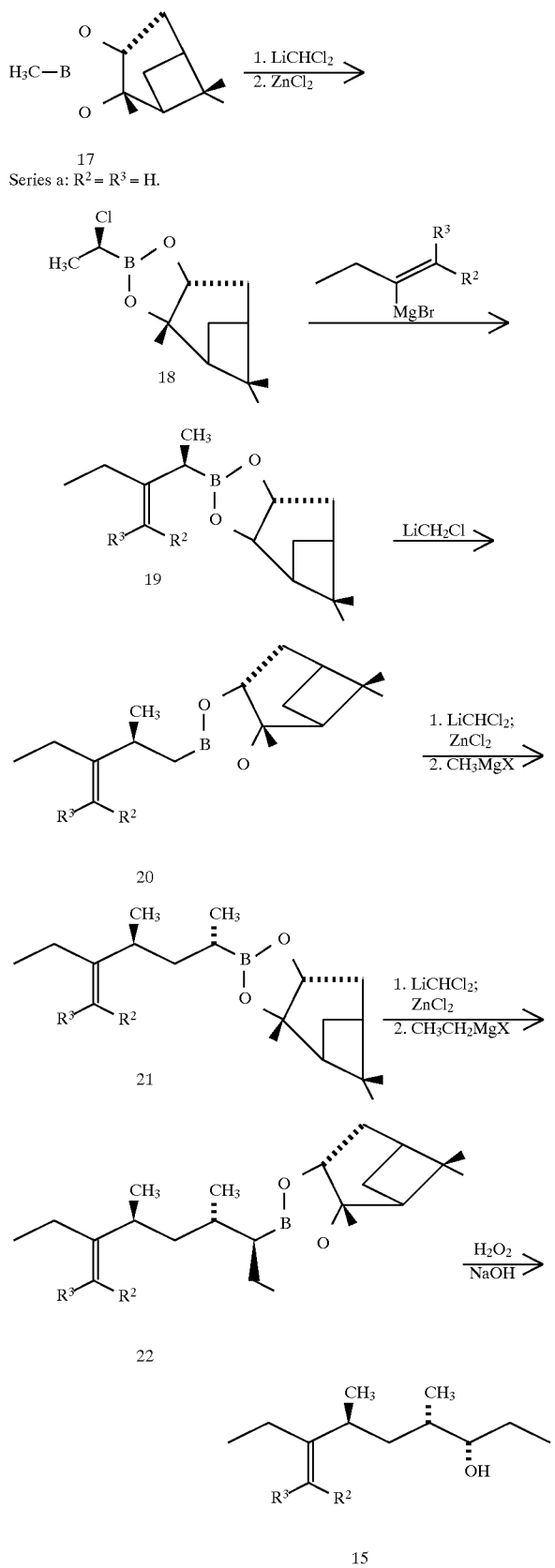

An important feature of this invention is the use of the unsaturated alcohol 15 as the immediate precursor to serricornin. The double bond can be cleaved to provide the ketone group of serricornin under mild conditions. In addition to the procedure with osmium tetroxide and sodium periodate described, carbon-carbon double bonds can generally be cleaved by ozonolysis or by permanganate. As is typical of 1,5-hydroxyketones, serricornin is isolated as an equilibrium mixture of the hydroxyketone 1 and its cyclic hemiacetal tautomer 2 [Mori, K. and Watanabe, H., Tetrahedron, 1985, 41:3423–3428]. The hemiacetal is very easily dehydrated by small amounts of acid to form the inactive cyclic enol ether 23.

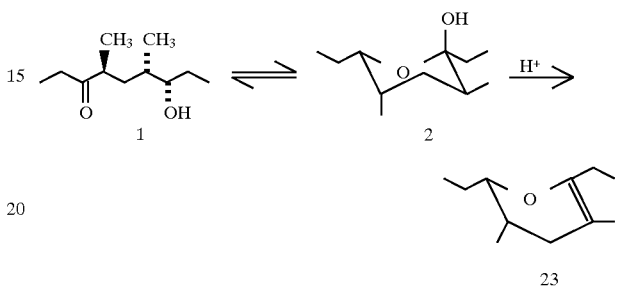

Although [S-(R*,R*,R*)]-2-ethyl-3,5-dimethyl-1-octen-6-ol 15a (=15, $R^2=R^3=H$) has been chosen as a practical and economical intermediate for reducing this invention to practice, it is readily apparent that other examples of 15 in which $R^2$ and/or $R^3$ are alkyl or aryl groups will similarly function as precursors to serricornin. A practical requirement is that the precursor to the Grignard reagent 8 (or an equivalent organometallic reagent such as an organolithium reagent), which may be described in general as a 3-halo-3-alkene or a 1-ethyl-1-halo-1-alkene, be economically accessible in high regioisomeric purity.

EXAMPLES

General

The usual procedures for handling reactive organometallic reagents were followed, including the use of an inert atmosphere (argon) and THF (tetrahydrofuran) that had been rigorously dried over sodium benzophenone ketyl.

[4R-(4α,5β)]-4,5-Dicyclohexyl-2-methyl-1,3,2-dioxaborolane (6)

This compound was prepared from [(R)-(R*,R*)]-1,2-dicyclohexyl-1,2-ethanediol and trimethyl boroxine by the previously reported method [Matteson, D. S. and Man, H.-W., J. Org. Chem., 1994, 59:5734–5741].

[4R-[2(S*),4α,5β]]-4,5-Dicyclohexyl-2-(1-chloroethyl)-1,3,2-dioxaboro-lane (7)

The previously described procedure [Matteson, D. S. and Sadhu, K. M., U.S. Pat. No. 4,525,309, Jun. 25, 1985; Matteson, D. S. et al., J Am. Chem. Soc., 1986, 108:812–819] was used for the preparation of (dichloromethyl)lithium (76 mmol) from a solution of dichloromethane (12.9 g, 150 mmol) in THF (tetrahydrofuran) (200 mL) and butyllithium (47.5 mL of 1.6 M solution in hexane, 76 mmol) at −100° C. After 5 min, a solution of [4R-(4α,5β)]-4,5-dicyclohexyl-2-methyl -1,3,2-dioxaborolane (6) (18.0 g, 72 mmol) in THF (100 mL) was added via cannula to the stirred mixture. Anhydrous zinc chloride (7.8 g, 58 mmol) was added. The solution was allowed to warm to 20°–25° C. and stirred for 24 h. The solvent was removed under vacuum. Ether (300 mL) was added and the mixture was washed with saturated ammonium chloride solution (3∞200 mL). The organic phase was dried over anhydrous magnesium sulfate (5 g) and filtered. Concentration at reduced pressure yielded [4R-[2(S*),4α,5β]]-4,5-dicyclohexyl-2-(1-chloroethyl)-1,3,2-dioxaborolane (7)(21.2 g, 98%); 300 MHz $^1$H-NMR (CDCl$_3$) δ0.88–1.79 (m,22), 1.55 (d, 3), 3.453 (q, J=7.5 Hz, 1), 3.82–3.96 (m, 2); 75 MHz $^{13}$C-NMR (CDCl$_3$) δ20.6, 25.7, 25.9, 26.3, 27.1, 28.0, 37.9, 42.7, 84.0. HRMS: calcd for $C_{16}H_{28}BClO_2$ (M+) 298.1871, found 298.1864.

2-Bromo-1-Butene

1-Butyne (21.63 g, 31.9 mL, 400 mmol) was condensed in a flask at –78° C. under argon and boron tribromide (100.2 g, 37.81 mL, 400 mmol) was added dropwise. An exothermic reaction occurred, with the evolution of white fumes. After addition of boron tribromide the neat reaction mixture was stirred at –78° C. for 0.5 h. Pentane (1 L) was added slowly at –78° C. The resulting orange homogeneous solution was poured slowly onto excess crushed ice (CAUTION: Hydrogen bromide evolution occurs). The pentane solution was separated, the aquous phase was extracted with pentane (250 mL), and the combined pentane solution was concentrated to ~300 mL, then treated with glacial acetic acid (24 mL). The mixture was stirred at 20°–25° C. for 24 h or under reflux for 16 h. Excess acetic acid was neutralized with sodium carbonate solution and washed with water (2∞300 mL). The solution was dried over anhydrous magnesium sulfate, filtered, and concentrated under reduced pressure. 2-Bromo-1-butene was distilled under vacuum (pump capable of 1 torr) from a flask immersed in a bath at <10° C. into a receiver cooled with a –78° C. bath (37.85 g, 70%); 300 MHz $^1$H-NMR (CDCl$_3$) δ1.11 (t, 3), 2.44 (q, 2), 5.33 (s, 1), 5.52 (d, 1); 75 MHz $^{13}$C-NMR (CDCl$_3$) δ13.0, 34.9, 114.9, 136.1. HRMS: calcd for $C_4H_7Br$ (M+) 133.9731, found 133.9713.

Bromo(1-ethylethenyl)magnesium [1-Buten-2-ylmagnesium bromide](8a)

This Grignard reagent was prepared in the usual manner from magnesium turnings (3.2 g, 113 mmol) in THF (tetrahydrofuran) (250 mL) and a solution of 2-bromo-1-butene (13.5 g, 100 mmol) in THF (50 mL) was added slowly. The concentration of 8 was determined by titration with 2-propanol in THF using 1,10-phenanthroline as an indicator.

[4R-[2(R*),4α,5β]]-4,5-Dicyclohexyl-2-(2-ethyl-3-methylpropen-3-yl)-1,3,2-dioxaborolane (9a)

(1-Buten-2-yl)magnesium bromide (8a) (3.25 M in THF, 60 mmol) was added dropwise in 0.5 h to [4R-[2(S*),4α,5β]]-4,5-dicyclohexyl -2-(1-chloroethyl)-1,3,2-dioxaborolane (7) (17.88 g, 60 mmol) in THF (65 mL) stirred at –78° C. The bath was allowed to warm to 20°–25° C. and the reaction mixture was stirred for 20 h. The solution was concentrated under vacuum and ether (300 mL) was added to the residue. The ether solution was washed with saturated aqueous ammonium chloride (2∞200 mL), dried over anhydrous magnesium sulfate (3 g), filtered, and concentrated at reduced pressure to colorless liquid 9 (18.13 g, 95%); 300 MHz $^1$H-NMR (CDCl$_3$) δ0.80–1.77 (m, 22), 1.04 (d, 3), 1.17 (t, 3), 1.90 (q, 1), 2.00 (m, 1), 2.10 (m, 1), 3.83 (d, 2), 4.72+4.73 (AB, 2); 75 MHz $^{13}$C-NMR (CDCl$_3$) ppm 12.3, 14.8, 25.9, 25.9, 26.4, 27.3, 28.12, 29.3, 43.0, 83.3, 105.5, 154.0. HRMS: calcd for $C_{20}H_{35}BO_2$ (M+) 318.2730, found: 318.2742.

[4R-[2(S*),4α,5β]]-4,5-Dicyclohexyl-2-(2-ethyl-3-methylbuten-4-yl)-1,3,2-dioxaborolane (10a)

Butyllithium (1.6 M in hexane, 40 mL, 64 mmol) was added slowly from a syringe to a stirred solution of [4R-[2(R*),4α,5↑]]-4,5-dicyclohexyl -2-(2-ethyl-3-methylpropen-3-yl)-1,3,2-dioxaborolane (9a) (17.8 g, 56 mmol) and chloroiodomethane (21.16 g, 8.73 mL, 120 mmol) in THF (200 mL) cooled with a –78° C. bath. The bath was allowed to warm to 20°–25° C. and the mixture was stirred for 24 h. The solution was concentrated under vacuum and ether (300 mL) was added. The ether solution was washed with saturated aqueous ammonium chloride (2∞200 mL), dried over anhydrous magnesium sulfate, filtered, and concentrated under reduced pressure to liquid [4R-[2(S*), 4α,5β]]-4,5-dicyclohexyl-2-(2-ethyl -3-methylbuten-4-yl)-1,3,2-dioxaborolane (10a) (17.6 g, 95%); 300 MHz $^1$H-NMR (CDCl$_3$) δ0.89–1.77 (m, 30), 2.03–2.06 (m, 2), 2.39 (m, 1), 3.80–3.85 (m, 2), 4.63 (d, 1), 4.72 (m, 1); 75 MHz $^{13}$C-NMR (CDCl$_3$) δ12.2, 17.9, 22.7, 25.8, 25.9, 26.3, 27.2, 28.3, 35.7, 42.9, 82.1, 105.0, 157.6. HRMS: calcd for $C_{21}H_{37}BClO_2$ (M+) 332.2889, found 332.2881.

[4R-[2(S*,S*),4α,5β]]-4,5-Dicyclohexyl-2-(5-chloro-2-ethyl-3-methyl-penten-5-yl)-1,3,2-dioxaborolane (11a)

A solution of [4R-[2(S*),4α,5β]]-4,5-dicyclohexyl-2-(2-ethyl-3-methylbuten-4-yl)-1,3,2-dioxaborolane (10a) (14.9 g, 45 mmol) in THF (50 mL) was added via cannula to (dichloromethyl)lithium (50 mmol) at –100° C. as described under the preparation of 7. Anhydrous zinc chloride (6.13 g, 45 mmol) was added, the bath was allowed to warm to 20°–25° C., and the mixture was stirred for 24 h. The solution was concentrated under vacuum and the residue was dissolved in ether (300 mL). The solution was washed with saturated aqueous ammonium chloride (3∞200 mL) and the organic phase was dried over magnesium sulfate (3 g), filtered, and concentrated to liquid [4R-[2(S*,S*),4α,5β]]-4,5-dicyclohexyl-2-(5-chloro-2-ethyl-3-methylpenten-5-yl)-1,3,2-dioxaborolane (11) (16.5 g, 97%); 300 MHz $^1$H-NMR (CDCl$_3$): δ0.80–2.09 (m, 32), 2.52–2.55 (m, 1), 3.48 (dd, 1), 3.92 (m, 2), 4.79 (m, 2); 75 MHz $^{13}$C-NMR (CDCl$_3$): ppm 12.2, 20.5, 25.5, 25.8, 25.9, 26.3, 27.2, 28.1, 37.7, 39.5, 42.9, 84.1, 108.2, 153.8. HRMS: calcd for $C_{22}H_{38}BClO_2$ (M+) 380.2653, found 380.2629.

[4R-[2(S*,S*),4α,5β]]-4,5-Dicyclohexyl-2-(2-ethyl-3,5-dimethylpenten-5-yl)-1,3,2-dioxaborolane (12a)

Methylmagnesium bromide (3.0 M in ether, 13.3 mL, 40 mmol) was added to a stirred solution of [4R-[2(S*,S*),4α,5β]]-4,5-dicyclohexyl-2-(5-chloro-2-ethyl-3-methylpenten-5-yl)-1,3,2-dioxaborolane (15.2 g, 40 mmol) in THF (250 mL) at –78° C. over a period of 20 min. The bath was allowed to warm to 20°–25° C. and the reaction mixture was stirred for 20 h. The solution was concentrated under vacuum and ether (200 mL) was added to the residue. The ethereal solution was washed with saturated aqueous ammonium chloride (2∞200 mL), dried over anhydrous magnesium sulfate, filtered, and concentrated under vacuum to liquid [4R-[2(S*,S*),4α,5β]]-4,5-dicyclohexyl-2-(2-ethyl-3,5-dimethylpenten-5-yl)-1,3,2-dioxaborolane (12a) (13.8 g, 96%); 300 MHz $^1$H-NMR (CDCl$_3$) δ0.84–2.27 (m, 37), 3.81 (m, 2), 4.68 and 4.74 (AB, 2); 75 MHz $^{13}$C-NMR (CDCl$_3$) 12.3, 16.2, 20.2, 25.9, 26.0, 26.4, 27.4, 28.28, 28.34, 39.2, 39.5, 43.0, 83.2, 106.7, 156.3). HRMS: calcd for $C_{23}H_{41}BO_2$ (M+) 360.3200, found: 360.3199.

[4R-[2(S*,S*,S*),4α,5β]]-4,5-Dicyclohexyl-2-(6-chloro-2-ethyl-3,5-di-methylhexen-6-yl)-1,3,2-dioxaborolane (13a)

A solution of [4R- [2(S*,S*),4α,5β]]-4,5-dicyclohexyl-2-(2-ethyl-3,5-dimethylpenten-5-yl)-1,3,2-dioxa-borolane (12a) (13.66 g, 37.94 mmol) in THF (50 mL) was added via cannula to (dichloromethyl)lithium (48 mmol) at −100° C. as described under the preparation of 7. Anhydrous zinc chloride (5.2 g, 38 mmol) was added, the bath was allowed to warm to 20°–25° C., and the mixture was stirred for 24 h. The solution was concentrated under vacuum and ether (300 mL) was added to the residue. The ethereal solution was washed with saturated aqueous ammonium chloride (3∞200 mL), dried over anhydrous magnesium sulfate (3 g), filtered, and concentrated under vacuum to liquid [4R-[2 (S*,S*,S*),4α,5β]]-4,5-dicyclohexyl -2-(6-chloro-2-ethyl-3,5-dimethylhexen-6-yl)-1,3,2-dioxaborolane (13a) (15.17 g, 98%); 300 MHz $^1$H-NMR (CDCl$_3$): δ0.85–2.22 (m, 37), 3.45 (d, 1), 3.93 (m, 2), 4.70 and 4.72 (AB, 2); 75 MHz $^{13}$C-NMR (CDCl$_3$): δ12.3, 17.1, 19.7, 25.3, 25.9, 25.9, 26.3, 27.3, 28.2, 34.2, 37.5, 40.3, 42.9, 84.0, 107.1, 156.1. HRMS: calcd for $C_{24}H_{42}BClO_2$ (M+) 408.2966, found 408.2968.

[4R-[2(S*,S*,S*),4α,5β]]-4,5-Dicyclohexyl-2-(2,6-diethyl-3,5-dimethyl-hexen-6-yl)-1,3,2-dioxaborolane (14a)

Ethylmagnesium bromide (3.0 M in diethyl ether, 35.6 mmol) was added dropwise in 20 minutes to a stirred solution of [4R- [2(S*,S*,S*),4α,5β]]-4,5-dicyclohexyl-2-(6-chloro-2-ethyl-3,5-dimethylhexen-6-yl) -1,3,2-dioxaborolane (14.5 g, 35.6 mmol) in THF (200 mL) cooled with a −78° C. bath. The bath was allowed to warm to 20°–25° C. and the mixture was stirred for 24 h. The solution was concentrated under vacuum and ether (200 mL) was added to the residue. The ethereal solution was washed with saturated aqueous ammonium chloride (2∞200 mL), dried over anhydrous magnesium sulfate, filtered, and concentrated under vacuum to liquid [4R-[2(S*,S*,S*),4α,5β]]-4,5-dicyclohexyl -2-(2,6-diethyl-3,5-dimethylhexen-6-yl)-1,3,2-dioxaborolane (14a) as a liquid (12.9 g, 90%); 300 MHz $^1$H-NMR (CDCl$_3$) δ0.87–2.27 (m, 43), 3.81 (m, 2), 4.66 and 4.71 (AB, 2); 75 MHz $^{13}$C-NMR (CDCl$_3$): 12.3, 14.1, 17.6, 19.5, 22.0, 25.8, 25.9, 26.1, 27.1, 27.6, 28.2, 28.5, 31.6, 37.4, 43.1, 83.1, 105.8, 156.8. HRMS: calcd for $C_{26}H_{48}BO_2$ [(M+1)+] 403.3747; found, 403.3732.

[S-(R*,R*,R*)]-2-Ethyl-3,5-dimethyl-1-octen-6-ol (15a)

Aqueous 3M sodium hydroxide (30 mL) and a solution of [4R-[2(S*,S*,S*),4α,5β]]-4,5 -dicyclo-hexyl-2-(2,6-diethyl-3,5-dimethylhexen-6-yl)-1,3,2-dioxaborolane (14a) (4.02 g, 10 mmol) in diethyl ether (200 mL) were stirred and cooled with an ice bath during the portionwise addition of 30% hydrogen peroxide (30 mL) over a period of 1 h. The mixture was stirred for 15 h, more ether (100 mL) was added, and the ether phase was washed with water (2∞100 mL), dried over anhydrous magnesium sulfate (1 g), and filtered. Concentration at 50 torr yielded a residue consisting of [S-(R*,R*,R*)-]2-ethyl-3,5-dimethyl-1-octen-6-ol (15a, $R^2=R^3=H$) and [(R)-(R*,R*)]-1,2-dicyclohexyl-1,2-ethanediol. The latter was recovered by addition of pentane (25 mL) and crystallization at 0° C. Chromatography on silica with 9:1 pentane/ether yielded pure 15a (1.62 g, 89%), $[α]^{22}_{Hg546}$ −12.5° (c=2.3, CHCl$_3$); 300 MHz $^1$H-NMR (CDCl$_3$) δ0.83–2.30 (m, 20), 3.4 (m, 1), 4.75 (d, 2); 75 MHz $^{13}$C-NMR (C$_6$D$_6$) δ10.5, 12.3, 13.3, 19.8, 26.5, 29.6, 35.0, 37.4, 40.2, 75.9, 106.3, 156.6. HRMS: calcd for $C_{12}H_{21}$ [(M−19)+] 165.1644; found, 165.1621.

Serricornin (1+2)

Osmium tetraoxide (80 mg, 0.3 mmol) was added to a solution of [S-(3R*,5R*,6R*)-2-ethyl-3,5-dimethyl-1-octen-6-ol (15a) (0.552 g, 3 mmol) in 36 mL of 1,4-dioxane and 12 mL of water at 20°–25° C. After 15 min, finely powdered sodium periodate (10.0 g, 46.8 mmol) was added in several portions over a period of 1 h, in accord with the literature procedure [Pappo, R. et al., *J. Org. Chem.*, 1956, 21:478–479]. The mixture was stirred for 16 h, then extracted with ether (2∞50 mL). The ether solution was washed with sodium sulfite solution, dried over anhydrous magnesium sulfate (0.5 g), filtered, and concentrated at 50 torr to yield a residue of serricornin (1 and 2) (0.507 g, 91%). The NMR data are consistent with those previously reported [Mori, K. and Watanabe, H., *Tetrahedron*, 1985, 41:3423–3428]:300 MHz $^1$H-NMR (C$_6$D$_6$) (literature data in parentheses) δ0.8–2.4 (m, 23), 3.2 (lit 3.17) (m, 0.75, CH—O of 2), 3.75 (lit 3.82) (ddd, 0.25, CH—O of 1); 75 MHz $^{13}$C-NMR (C$_6$D$_6$), assigned to 1:δ8.0, 10.7, 14.0, 16.5, 27.0, 33.9, 36.1, 36.8, 43.6, 76.4, 213.4 (8.0, 10.8, 13.7, 16.4, 27.5, 33.9, 35.8, 36.8, 43.8, 76.4, 213.6); assigned to 2:7.4, 10.7, 11.7, 16.8, 26.2, 30.2, 31.3, 33.1, 36.1, 72.6, 98.5 (7.4, 10.7, 11.7, 16.7, 26.2, 30.2, 31.3, 33.1, 36.2, 72.7, 98.6), HRMS: calcd for $C_{11}H_{20}O$ [(M−18)+] 168.1514; found, 168.1506.

Alternate Route to 15a via Pinanediol Esters 17–22a (S)-Pinanediol (1S)- (1-chloroethyl)boronate (18) was prepared by the published method [Matteson, D. S. et al., *J Am. Chem. Soc.*, 1986, 108:812–819]. Reaction of 18 with bromo(1-ethylethenyl)magnesium (8a) was carried out in a similar manner to that described above for the reaction of 7 with 8a to make 9a. The (S)-pinanediol [2-ethyl-(1-buten-3-yl)]boronate (19a) obtained after running the reaction mixture through a short silica column to remove inorganic salts and concentration contained 5% pinanediol (1-ethylethenyl)boronate as a contaminant according to NMR analysis; data for 19a: $^1$H NMR (CDCl$_3$) δ0.83 (s, 6) 1.04 (t, 5), 1.15 (d, 3), 1.2 (s, 6), 1.36 (s, 3), 1.4 (d, 2) 1.7–2.4 (m) 4.2 (dd, 1), 4.7 (m, 1), 4.75 (q, 1); $^{13}$C NMR (CDCl$_3$): δ12.4, 14.8, 24.0, 26.3, 27.0, 28.4, 29.5, 35.6, 39.4, 51.2, 77.7, 85.5, 127.7, 154.1; HRMS: calcd for $C_{16}H_{27}BO_2$ (M+) 262.2104; found, 262.2111. Conversion of 19a to (S)-pinanediol [2-ethyl-3-methyl-(1-buten-4-yl)]boronate (20a) was done under conditions similar to those used to convert 9a to 10a; data for 20a: $_1$H-NMR (CDCl$_3$): δ0.85 (s, 3) 1.03 (t, 3), 1.08 (d, 3), 1.42 (s, 3), 1.56 (d, 3) 1.7–2.4 (m, 3), 3.6 (q, 1), 4.25 (dd, 1), 4.65 (q, 1), 4.8 (m, 1), $^{13}$C NMR (CDCl$_3$, RT): d 12.44,19.33, 22.73, 24.00, 26.51, 28.69, 32.13, 35.26, 35.95, 39.49, 51.18, 69.79, 78.08, 105.38, 158.01. HRMS: calcd for $C_{17}H_{29}BO_2$ (M+) 276.2261; found, 276.2265. Conversion of 20a to (S)-pinanediol [2-ethyl-3-methyl-(1-hexen-5-yl)]boronate (21a) was done in a manner similar to the conversion of 10a to 12a, data for crude intermediate (S)-pinanediol [2-ethyl-5-chloro-3-methyl-(1 -penten-5-yl)] boronate (not illustrated): $^1$H-NMR (CDCl$_3$, RT): δ0.8–2.5 (m), 2.6 (m, 1), 3.42 (dd, 1), 4.30 (dd, 1), 4.6 (m, 2), $^{13}$C NMR (CDCl$_3$) δ12.3, 19.01, 20.6, 23.94, 26.4, 26.98, 28.43, 35.23, 37.47, 37.81, 39.38, 40.01, 51.46, 78.41, 86.59, 108.15, 153.87; HRMS: calculated for $C_{18}H_{30}BO_2Cl$ (M+) 324.2027, found 324.2019; data for 21a: $^1$H-NMR (CDCl$_3$): δ0.8–2.5 (m), 1.78 (m, 2), 2.6 (m, 1), 3.44 (dd, 2), 4.3 (dd, 1), 4.6 (m, 1), 4.7 (m, 1); $^{13}$C NMR (CDCl$_3$) δ12.3, 16.01, 20.1, 23.96, 25.6, 26.39, 27.06, 28.6, 35.42, 35.6, 38.1, 39.3, 39.4, 51.22, 77.58, 85.14, 106.45, 156.35; HRMS calcd for $Cl_9H_{33}BO2$ (M+) 304.2574; found, 304.2550. Conversion of 21a to (S)-pinanediol [2-ethyl-3,5- dimethyl-(1-octen-6-yl)]boronate (22a) was carried out in a similar manner to that described for 12a to 14a, data for intermediate (S)- pinanediol [2-ethyl-6-chloro-3, 5-dimethyl-(1-hexen-6-yl)] boronate: $^1$H-NMR (CDCl$_3$): d 0.8–2.5 (m) 2.6 (m, 1), 3.42 (d, 1), 4.30 (dd, 1), 4.6 (m, 2); $^{13}$C NMR (CDCl$_3$) δ153.87, 108.15, 86.59, 78.4151.46, 40.01, 39.38, 37.81, 37.47, 35.23, 28.43, 26.98, 26.40, 23.94, 20.6, 12.3; data for 22a: $^{13}$C NMR (CDCl$_3$) δ156.13, 106.38, 85.26, 78.43, 77.56, 67.8, 51.1, 51.0, 39.46, 38.1, 37.5, 34.1, 28.6, 27.1, 26.5, 25.9, 23.9, 19.85, 17.1, 12.4, 7.8. Conversion of 22a to 15a was carried out with hydrogen peroxide in the same manner as the conversion of 14a to 15a.

While the preferred embodiment of the invention has been illustrated and described, it will be apparent that various changes can be made therein without departing from the spirit and scope of the invention.

LITERATURE CITED

Kuwahara, Y., Fukami, H., Howard, R., Ishii, S., Matsumura, F., and Burkholder, W.E., *Tetrahedron*, 1978, 34:1769–1774.

Mori, M., Mochizuki, K., Kohno, M., Chuman, T., Ohnishi, A., Watanabe, H., and Mori, K., *J. Chem. Ecol.*, 1985, 12:83–89.

Mori, K. and Watanabe, H., *Tetrahedron*, 1985, 41:3423–3428.

Matteson, D. S. and Sadhu, K. M., U.S. Pat. No. 4,525,309, Jun. 25, 1985.

Tripathy, P. B. and Matteson, D. S., *Synthesis*, 1990, 200–206.

Matteson, D. S., Sadhu, K. M. and Peterson, M. L., *J Am. Chem. Soc.*, 1986, 108:812–819.

Sadhu, K. M. and Matteson, D. S., *Organometallics*, 1985, 4:1687–1689.

Pappo, R., Allen, D. S., Jr., Lemieux, R. U., and Johnson, W. S., *J Org. Chem.*, 1956, 21:478–479

What is claimed is:

1. A process for preparing serricomin in high diastereomeric and enantiomeric purity, comprising oxidizing an [S-(R*,R*,R *)]-7-alkylidene-4, 6-dimethyl-3-nonanol to obtain serricornin.

2. The process of claim 1 wherein [S-(R*,R*,R*)]-7-alkylidene-4, 6-dimethyl-3-nonanol is [S-(R*,R*,R*)]-2-ethyl-3,5-dimethyl-1-octen-6-ol.

3. The process of claim 1 in which the [S-(R*,R*,R*)]-7-alkylidene-4, 6-dimethyl-3-nonanol is oxidized by reaction with sodium periodate in the presence of a catalytic amount of osmium tetroxide.

4. A process for the preparation of a [S-(R*,R*,R*)]-7-alkylidene-4, 6-dimethyl-3-nonanol in high diastereomeric and enantiomeric purity, comprising reacting a [4R-[2(S*), 4α,5β]]-4,5-dialkyl-2-(1-haloethyl)-1,3,2-dioxaborolane or a pinandiol boronic ester with a 1-ethyl-1-metallo-1-alkene in order to make a carbon—carbon bond in a stereocontrolled manner, followed by stereoselective carbon chain extension to obtain the desired [S-(R*,R*,R*)]-7-alkylidene-4,6-dimethyl-3-nonanol.

5. The process of claim 4 wherein the [S-(R*,R*,R*)]-7-alkylidene-4, 6-dimethyl-3-nonanol is [S-(R*,R*,R*)-]2-ethyl-3,5-dimethyl-1-octen-6-ol and the 1-ethyl-1-metallo-1-alkene is a 1-ethyl-1-metalloethene.

6. The process of claim 4 wherein the [4R-[2(S*),4α, 5β]]-4,5-dialkyl -2-(1-haloethyl)-1,3,2-dioxaborolane is reacted with the 1-ethyl-1-metallo-1-alkene and the [4R-[2 (S*),4α,5β]]-4,5-dialkyl-2-( 1-haloethyl)-1,3,2-dioxaborolane is [4R-[2(S*),4α,5β]]-4,5-dicyclohexyl-2-(1-chloroethyl)-1,3,2-dioxaborolane.

7. The compound [S-(R*,R*,R *)]-2-ethyl-3,5-dimethyl-1-octen-6-ol.

* * * * *

UNITED STATES PATENT AND TRADEMARK OFFICE
CERTIFICATE OF CORRECTION

Page 1 of 7

PATENT NO. : 5,817,882
DATED : October 6, 1998
INVENTOR(S) : D.S. Matteson et al.

It is certified that error appears in the above-identified patent and that said Letters Patent is hereby corrected as shown below:

| COLUMN | LINE | |
|---|---|---|
| [56]<br>Pg. 1, col. 2 | Refs. Cited<br>(Other Publs.,<br>Item 6) | before "J." insert a space |
| [57]<br>Pg. 1, col. 2 | Abstract<br>5 of text | "[,S" should read --[S-- |
| 1 | 7 | "1996,now" should read --1996, now-- |
| 1 | 12 | "serricomin" should read --serricornin-- |
| 1 | 23 | "serricomin." should read --serricornin.-- |
| 1 | 23 | "Serricomin" should read --Serricornin-- |
| 1 | 35 | "serricomin" should read --serricornin-- |
| 1 | 53 | "serricomin" should read --serricornin-- |
| 2 | 5 | "SUMMARV" should read --SUMMARY-- |
| 2 | 36 | "serricomin" should read --serricornin-- |
| 3 | Formula 10 | after "LiCHCl$_2$" insert a semicolon |
| 3 | Formula 15 | "NalO$_4$" should read --NaIO$_4$-- |

UNITED STATES PATENT AND TRADEMARK OFFICE
CERTIFICATE OF CORRECTION

PATENT NO. : 5,817,882
DATED : October 6, 1998
INVENTOR(S) : D.S. Matteson et al.

It is certified that error appears in the above-identified patent and that said Letters Patent is hereby corrected as shown below:

COLUMN  LINE

4  Formula 16  " 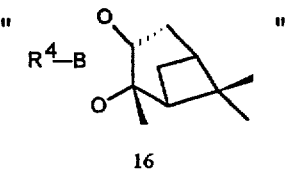 should read

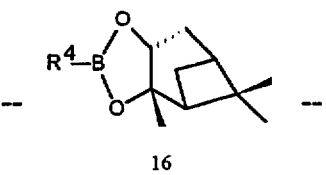

4  18-19  "serricomin" should read --serricornin--

4  19  "serricomin" should read --serricornin--

4  60  "di-cyclohexyl" should read --dicyclohexyl--

5  10  "etal." should read --et al.--

6  66  "serricomin" should read --serricornin--

UNITED STATES PATENT AND TRADEMARK OFFICE
CERTIFICATE OF CORRECTION

Page 3 of 7

PATENT NO. : 5,817,882
DATED : October 6, 1998
INVENTOR(S) : D.S. Matteson et al.

It is certified that error appears in the above-identified patent and that said Letters Patent is hereby corrected as shown below:

COLUMN     LINE

7     Formula 17    "  "    should read

-- 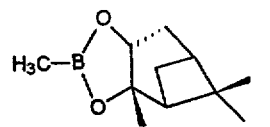 --

7     Formula 20    " 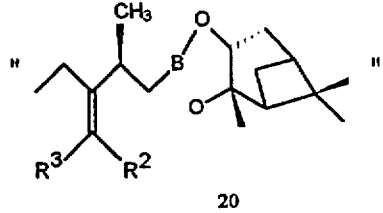 "    should read

-- 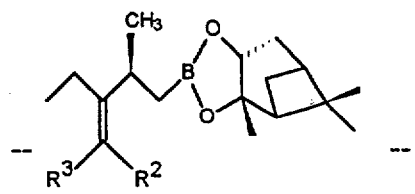 --

UNITED STATES PATENT AND TRADEMARK OFFICE
CERTIFICATE OF CORRECTION

PATENT NO. : 5,817,882
DATED : October 6, 1998
INVENTOR(S) : D.S. Matteson et al.

It is certified that error appears in the above-identified patent and that said Letters Patent is hereby corrected as shown below:

COLUMN     LINE

7     Formula 22     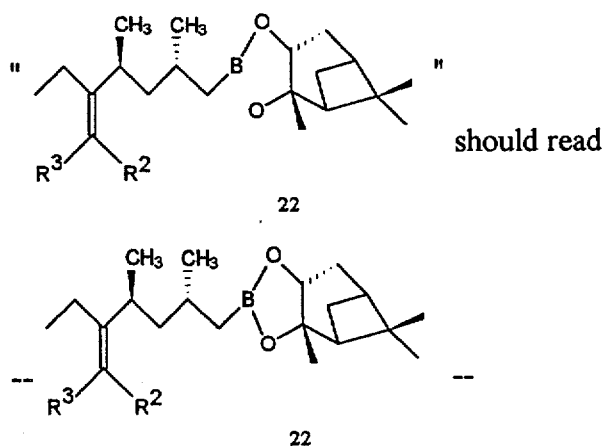 should read

| COLUMN | LINE |  |
|---|---|---|
| 9 | 7 | "(7)(21.2 g, 98%)" should read --(7) (21.2 g, 98%)-- |
| 9 | 11 | "(M+)" should read --($M^+$)-- |
| 9 | 23 | "aquous" should read --aqueous-- |
| 9 | 36 | "(M+)" should read --($M^+$)-- |
| 9 | 39 | "ylmagnesium" should read --yl magnesium-- |
| 9 | 39 | "bromide1](8a)" should read --bromide] (8a)-- |
| 9 | 66 | "(M+)" should read --($M^+$)-- |

UNITED STATES PATENT AND TRADEMARK OFFICE
CERTIFICATE OF CORRECTION

PATENT NO. : 5,817,882
DATED : October 6, 1998
INVENTOR(S) : D.S. Matteson et al.

It is certified that error appears in the above-identified patent and that said Letters Patent is hereby corrected as shown below:

| COLUMN | LINE | |
|---|---|---|
| 10 | 5 | "5↑" should read --5β-- |
| 10 | 20 | "(M+)" should read --(M$^+$)-- |
| 10 | 42 | "(M+)" should read --(M$^+$)-- |
| 10 | 62 | "(M+)" should read --(M$^+$)-- |
| 10 | 64 | "di-methylhexen" should read --dimethylhexen-- |
| 10 | 67 | "dioxa-borolane" should read --dioxaborolane-- |
| 11 | 17 | "(M+)" should read --(M$^+$)-- |
| 11 | 19 | "dimethyl-hexen" should read --dimethylhexen-- |
| 11 | 40 | "[(M+1)+]" should read --[(M+1)$^+$]-- |
| 11 | 45 | "dicyclo-hexen" should read --dicyclohexen-- |
| 11 | 63 | "[(M-19)+]" should read --[(M-19)$^+$]-- |
| 12 | 13 | "41:3423-3428]:300" should read --41:3423-3428]: 300-- |
| 12 | 16 | "1:δ8.0," should read --1: δ8.0,-- |
| 12 | 19 | "2:7.4," should read --2: 7.4-- |

UNITED STATES PATENT AND TRADEMARK OFFICE
CERTIFICATE OF CORRECTION

PATENT NO. : 5,817,882
DATED : October 6, 1998
INVENTOR(S) : D.S. Matteson et al.

It is certified that error appears in the above-identified patent and that said Letters Patent is hereby corrected as shown below:

| COLUMN | LINE | |
|---|---|---|
| 12 | 21 | "[(M-18)+]" should read --[(M-18)$^+$]-- |
| 12 | 36 | "$^1$H NMR" should read --$^1$H-NMR-- |
| 12 | 38 | "$^{13}$C NMR" should read --$^{13}$C-NMR-- |
| 12 | 40 | "(M+)" should read --(M$^+$)-- |
| 12 | 44 | "$_1$H-NMR" should read --$^1$H-NMR-- |
| 12 | 46 | "$^{13}$C NMR" should read --$^{13}$C-NMR-- |
| 12 | 49 | "(M+)" should read --(M$^+$)-- |
| 12 | 55-56 | "$^{13}$C NMR" should read --$^{13}$C-NMR-- |
| 12 | 58 | "$C_{18}H_{30}BO_2Cl$ (M+)" should read --$C_{18}H_{30}BO_2Cl$ (M$^+$)-- |
| 12 | 61 | "$^{13}$C NMR" should read --$^{13}$C-NMR-- |
| 12 | 64 | "$C_{19}H_{33}BO2$ (M+)" should read --$C_{19}H_{33}BO_2$ (M$^+$)-- |
| 13 | 2 | "$^1$ H-NMR" should read --$^1$H-NMR-- |
| 13 | 3 | "$^{13}$C NMR" should read --$^{13}$C-NMR-- |
| 13 | 4 | "78.4151.46" should read --78.41, 51.46-- |

UNITED STATES PATENT AND TRADEMARK OFFICE
CERTIFICATE OF CORRECTION

PATENT NO. : 5,817,882
DATED : October 6, 1998
INVENTOR(S) : D.S. Matteson et al.

It is certified that error appears in the above-identified patent and that said Letters Patent is hereby corrected as shown below:

| COLUMN | LINE | |
|---|---|---|
| 13 | 6 | "$^{13}$C NMR" should read --$^{13}$C-NMR-- |
| 14 (Claim 1, | 2 line 1) | "serricomin" should read --serricornin-- |
| 14 (Claim 5, | 24 line 2) | ")-]2" should read --)]-2-- |

Signed and Sealed this

Tenth Day of August, 1999

Attest:

Q. TODD DICKINSON

Attesting Officer

Acting Commissioner of Patents and Trademarks